United States Patent [19]

Westland

[11] 4,185,152
[45] Jan. 22, 1980

[54] THIAZOLIDINYL ALKOXY PYRIDINES

[75] Inventor: Roger D. Westland, Ann Arbor, Mich.

[73] Assignee: Warner-Lambert Company, Morris Plains, N.J.

[21] Appl. No.: 185,437

[22] Filed: Sep. 30, 1971

[51] Int. Cl.$^2$ .......................................... C07D 417/12
[52] U.S. Cl. .................................. 546/284; 424/263
[58] Field of Search ................................... 260/294.80

[56] References Cited
PUBLICATIONS

Tondeur, Rene et al., C. A., vol. 62, 1965, p. 5264a.

Primary Examiner—Henry R. Jiles
Assistant Examiner—Mildred A. M. Crowder
Attorney, Agent, or Firm—Robert R. Adams; Edward J. Gall; George M. Richards

[57] ABSTRACT

2-[ω-(3-thiazolidinyl)alkoxy]pyridine compounds, also substituted in the 5-position by methyl, chlorine, bromine, or iodine, and acid-addition salts thereof, which are useful as antiradiation agents, and their production by reacting a 2-pyridyloxyalkylaminoethanethiol with formaldehyde or a reactive derivative thereof.

6 Claims, No Drawings

THIAZOLIDINYL ALKOXY PYRIDINES

SUMMARY AND DETAILED DESCRIPTION

The present invention relates to new pyridine compounds that are useful as pharmacological agents and to methods for their production. More particularly, the invention relates to new 2-[ω-(3-thiazolidinyl)alkoxy]-pyridine compounds having the formula

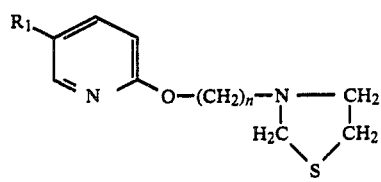

and to pharmaceutically-acceptable salts thereof; where $R_1$ is methyl, chlorine, bromine, or iodine, and n is a positive integer having a value of from 3 to 8, with said $R_1$ and n selected as follows: when $R_1$ is methyl, n is 5; when $R_1$ is chlorine, n is 4, 5, or 6; when $R_1$ is bromine, n is 3, 4, 5, 6, 7, or 8; and when $R_1$ is iodine, n is 4, 5, 6, or 7.

In accordance with the invention, 2-[ω-(3-thiazolidinyl)alkoxy]pyridine compounds having formula I above are produced by reacting a 2-pyridyloxyalkylaminoethanethiol compound having the formula

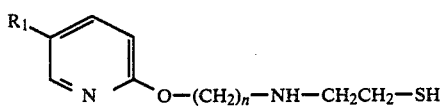

with formaldehyde or a reactive derivative thereof; where $R_1$ and n have the aforementioned significance. The formaldehyde may be used in the reaction in various forms, such as formalin, paraformaldehyde, and metaformaldehyde. It is preferably supplied to the reaction, however, as the reactive derivative, sodium formaldehyde bisulfite. The reaction is best carried out in an unreactive solvent medium. Suitable solvents include water, ethers, such as tetrahydrofuran, dioxane, diethylene glycol monomethyl ether, and diethylene glycol dimethyl ether, lower alkanols, such as methanol, ethanol, and 2-propanol, tertiary amides, such as N,N-dimethylformamide, dimethyl sulfoxide, and various mixtures of these. A preferred solvent medium is aqueous methanol. The temperature and duration of the reaction are not critical and may be varied widely, the temperature from 25° to 100° C. and the duration from 2 to 48 hours. The reaction is most conveniently carried out at the reflux temperature of the reaction mixture, or about 65° to 75° C., and at such temperature is essentially complete after 2 to 5 hours. While equivalent quantities of reactants may be employed, best results are obtained by using a large excess of the formaldehyde reactant. The reaction product may be isolated in free base or acid-addition salt form by appropriate adjustment of the pH of the reaction mixture.

The 2-pyridyloxyalkylaminoethanethiol compounds having formula II above that are used as starting materials in the foregoing process are prepared by reacting an aziridinylalkoxypyridine compound having the formula

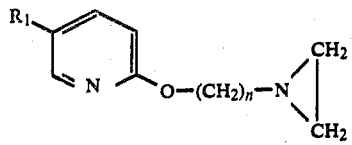

with hydrogen sulfide. The 2-pyridyloxyalkylaminoethanethiol compounds are normally prepared just prior to use in the foregoing process and are promptly reacted with a formaldehyde reactant as described above without isolation and characterization.

The aziridinylalkoxypyridine compounds having formula III above are prepared by reacting a 2-halopyridine compound having the formula $$R_1 \text{—pyridine—X} \quad \text{IV}$$

with an aziridinylalkanol compound having the formula $$\begin{array}{c} H_2C \\ | \\ H_2C \end{array} N\text{—}(CH_2)_n\text{—OH} \quad V$$

in the presence of sodium hydride; where each of $R_1$ and n has the same meaning as previously given and X is chlorine or bromine. The aziridinylalkanol compounds, in turn, are prepared by reacting an ω-chloroalkanol compound having the formula $$Cl\text{-}(CH_2)_n\text{-}OH \quad VI$$

with ethylenimine in the presence of a base such as potassium carbonate.

The compounds of the invention can exist in the free base form having formula I above or in the form of an acid-addition salt. Pharmaceutically-acceptable acid-addition salts are formed with any of a number of inorganic and organic acids, including hydrochloric, hydrobromic, hydriodic, sulfamic, benzenesulfonic, p-toluenesulfonic, citric, and succinic. A preferred acid-addition salt is the hydrochloride because of its ease of preparation. The acid-addition salts differ from the free base compounds with respect to certain physical properties such as solubility in polar solvents but are otherwise equivalent for the purposes of the invention.

The compounds of the invention are new chemical compounds that are useful as pharmacological agents, especially as antiradiation agents that are active in protecting against the effects of exposure to X-ray or gamma ray radiation. Their activity in this regard can be demonstrated and quantitatively measured in a standard test in experimental animals (mice) that is carried out essentially as described in a number of published reports; see, for example, R. D. Westland, et al., *J. Med. Chem.*, 11, 1190 (1968).

The results obtained in the antiradiation test for some representative compounds of the present invention are shown in the following table. In this table, the activity of each compound is expressed in terms of the percentage of animals that survived (30 days) the exposure to radiation at the given dose. The dose given is generally the lowest dose at which a high rate of survival was obtained. Administration was by the intraperitoneal route. Except where indicated otherwise, each compound was administered as the monohydrochloride salt to a test group consisting of 15 mice. The radiation dose was either 950 Roentgens supplied by a cobalt-60 gamma ray source or 825 Roentgens from an X-ray source.

ANTIRADIATION ACTIVITY $$R_1\text{-pyridine-}O-(CH_2)_n-N(CH_2CH_2SCH_2)$$

| $R_1$ | n | Approximate $LD_{50}$, mg./kg. | Dose mg./kg. | Pre-irradiation Time, min. | Survival, % |
|---|---|---|---|---|---|
| Br | 3 | 250 | 100 | 15 | 33 |
| Br | 5 | 240 | 180* | 30 | 100 |
|    |   |     | 90*  | 30 | 83  |
| Br | 8 | 230 | 50   | 30 | 20  |
| Cl | 5 | 160 | 80** | 15 | 87  |
|    |   |     | 80** | 30 | 93  |
| I  | 4 | >300| 100  | 15 | 20  |
| I  | 5 | 230 | 100  | 30 | 93  |
| I  | 7 | 200 | 100  | 30 | 47  |
| $CH_3$ | 5 | 190 | 70** | 30 | 33 |

*The test group consisted of six mice.
**Administered as the dihydrochloride salt.

The compounds of the invention can be administered either orally or parenterally and in free base or pharmaceutically-acceptable salt form. They can be combined with either a solid or liquid carrier or diluent and made available in varying amounts in such pharmaceutical forms as tablets, capsules, powders, and aqueous and non-aqueous suspensions and solutions.

The invention is illustrated by the following examples.

EXAMPLE 1

To a solution of 5.1 g. of hydrogen sulfide in 50 ml. of ethanol, cooled to −45° C., is added a solution of 13.0 g. of 2-[3-(1-aziridinyl)propoxy]-5-bromopyridine in ethanol, and the resulting solution is allowed to warm to room temperature and to stand for 2 hours before the solvent is evaporated under reduced pressure. The residue, which is 2-{{3-[(5-bromo-2-pyridyl)oxy]propyl}amino}ethanethiol, is dissolved in 50 ml. of methanol, the solution is combined with a solution of 67 g. of sodium formaldehyde bisulfite in 50 ml. of water, and the resulting reaction mixture is heated under reflux for 4 hours. The mixture is then concentrated under reduced pressure to remove the solvent, the residue is extracted well with ether, and the ether extract is dried and treated with excess dry hydrogen chloride to give an oily precipitate of 5-bromo-2-[3-(3-thiazolidinyl)-propoxy]pyridine, monohydrochloride, which is isolated and purified by crystallization twice from acetonitrile; m.p. 176°–179° C.

EXAMPLE 2

To a solution of 4 g. of hydrogen sulfide in 100 ml. of ethanol, cooled to −45° C., is added 10 g. of 2-[4-(1-aziridinyl)butoxy]-5-bromopyridine, and the resulting solution is allowed to warm to room temperature over a period of 2 hours before the solvent is evaporated under reduced pressure. The residue, which is 2-{{4-[(5-bromo-2-pyridyl)-oxy]butyl}amino}ethanethiol, is dissolved in 100 ml. of methanol, the solution is combined with a solution of 50 g. of sodium formaldehyde bisulfite in 100 ml. of water, and the resulting reaction mixture is stirred and heated under reflux for 4 hours, and then stirred overnight at room temperature. It is concentrated to remove the solvent, and the residue, which is 5-bromo-2-[4-(3-thiazolidinyl)-butoxy]pyridine, is mixed well with water. The aqueous mixture is extracted with ether and the ether extract is dried and mixed well with 9.2 ml. of 4 N isopropanolic hydrogen chloride to give a solid precipitate of 5-bromo-2-[4-(3-thiazolidinyl)butoxy]pyridine, monohydrochloride, which is isolated and purified by crystallization twice from acetonitrile; m.p. 151°–153° C.

EXAMPLE 3

Utilizing the general procedure described in Examples 1 and 2 above, the following 2-[ω-(3-thiazolidinyl)-alkoxy]pyridine compounds are obtained from the reactions indicated below.

(a) 5-Bromo-2-{[5-(3-thiazolidinyl)pentyl]oxy}-pyridine, monohydrochloride, m.p. 121°–124° C., following three crystallizations from acetonitrile; from the initial reaction of 17 g. of 2-{[5-(1-aziridinyl)pentyl]oxy}-5-bromopyridine with 6.1 g. of hydrogen sulfide in 30 ml. of ethanol, and the subsequent reaction of the intermediate 2-{{5-[(5-bromo-2-pyridyl)oxy]pentyl}amino}ethanethiol with 80 g. of sodium formaldehyde bisulfite in aqueous methanol to give the free base product, which is further reacted in ether solution with dry hydrogen chloride to give the monohydrochloride salt.

(b) 5-Bromo-2-{[6-(3-thiazolidinyl)hexyl]oxy}-pyridine, monohydrochloride, m.p. 124°–126° C., following three crystallizations from acetonitrile; from the initial reaction of 15 g. of 2-{[6-(1-aziridinyl)hexyl]oxy}-5-bromopyridine with 5.1 g. of hydrogen sulfide in ethanol, and the subsequent reaction of the intermediate 2-{{6-[(5-bromo-2-pyridyl)oxy]hexyl}amino}ethanethiol with 67 g. of sodium formaldehyde bisulfite in aqueous methanol to give the free base product, which is further reacted in ether solution with 2.3 N isopropanolic hydrogen chloride to give the monohydrochloride salt.

(c) 5-Bromo-2-{[7-(3-thiazolidinyl)heptyl]oxy}-pyridine, monohydrochloride, m.p. 131°–134° C., following crystallization from acetonitrile; from the initial reaction of 15.7 g. of 2-{[7-(1-aziridinyl)heptyl]oxy}-5-bromopyridine with 5 g. of hydrogen sulfide in ethanol, and the subsequent reaction of the intermediate 2-{{7-[(5-bromo-2-pyridyl)oxy]heptyl}amino}ethanethiol with 60 g. of sodium formaldehyde bisulfite in aqueous methanol to give the free base product, which is further reacted in ether solution with 5.3 N isopropanolic hydrogen chloride to give the monohydrochloride salt.

(d) 5-Bromo-2-{[8-(3-thiazolidinyl)octyl]oxy}-pyridine, monohydrochloride, m.p. 135°–136.5° C., following successive crystallizations from acetone and ethyl acetate; from the initial reaction of 10.4 g. of 2-{[8-(1-aziridinyl)-octyl]oxy}-5-bromopyridine with 3.1 g. of hydrogen sulfide in ethanol, and the subsequent reaction of the intermediate 2-{{8-[(5-bromo-2-pyridyl)oxy]octyl}amino}ethanethiol with 42.6 g. of sodium formaldehyde bisulfite in aqueous methanol to give the free base product, which is further reacted in ether solution with excess dry hydrogen chloride to give the monohydrochloride salt.

EXAMPLE 4

Utilizing the general procedure described in Examples 1 and 2 above, the following 2-[ω-(3-thiazolidinyl)-alkoxy]pyridine compounds are obtained from the reactions indicated below.

(a) 5-Chloro-2-[4-(3-thiazolidinyl)butoxy]pyridine, monohydrochloride, m.p. 110°–115° C., following crystallization from acetonitrile; from the initial reaction of 10 g. of 2-[4-(1-aziridinyl)butoxy]-5-chloropyridine with 4.4 g. of hydrogen sulfide in ethanol, and the subsequent reaction of the intermediate 2-{{4-[(5-chloro-2-pyridyl)oxy]butyl}-amino}ethanethiol with 59 g. of sodium formaldehyde bisulfite in aqueous methanol to give the free base product, which is further reacted in ether solution with 4 N isopropanolic hydrogen chloride to give the monohydrochloride salt.

(b) 5-Chloro-2-{[5-(3-thiazolidinyl)pentyl]-oxy}pyridine, dihydrochloride, m.p. 143°–145° C., following crystallization from ethanol; from the initial reaction of 24 g. of 2-{[5-(1-aziridinyl)pentyl]oxy}-5-chloropyridine with 10.2 g. of hydrogen sulfide in ethanol, and the subsequent reaction of the intermediate 2-{{5-[(5-chloro-2-pyridyl)oxy]pentyl}amino}ethanethiol with 134 g. of sodium formaldehyde bisulfite in aqueous methanol to give the free base product, which is further reacted in ether solution with excess dry hydrogen chloride to give the dihydrochloride salt.

(c) 5-Chloro-2-{[6-(3-thiazolidinyl)hexyl]-oxy}pyridine, monohydrochloride, m.p. 132°–135° C., following crystallization from acetonitrile; from the initial reaction of 15 g. of 2-{[6-(1-aziridinyl)hexyl]oxy}-5-chloropyridine with 6 g. of hydrogen sulfide in ethanol, and the subsequent reaction of the intermediate 2-{{6-[(5-chloro-2-pyridyl)oxy]hexyl}amino}ethanethiol with 63 g. of sodium formaldehyde bisulfite in aqueous methanol to give the free base product, which is further reacted in ether solution with 4 N isopropanolic hydrogen chloride to give the monohydrochloride salt.

EXAMPLE 5

To a solution of 4 g. of hydrogen sulfide in 30 ml. of methanol, cooled to −45° C., is added a solution of 12.8 g. of 2-[4-(1-aziridinyl)butoxy]-5-iodopyridine in 30 ml. of methanol, and the resulting solution is allowed to warm to room temperature during a period of 90 minutes before the solvent is evaporated under reduced pressure. The residue, which is 2-{{4-[(5-iodo-2-pyridyl)oxy]-butyl}amino}ethanethiol, is dissolved in 70 ml. of methanol, the solution is combined with a solution of 40 g. of sodium formaldehyde bisulfite in 70 ml. of water, and the resulting reaction mixture is heated under reflux for 4 hours. It is then concentrated to remove the solvent, and the residue is extracted with ether. The ether extract is washed well with water and dried. The dried ethereal solution is mixed with 17 ml. of 4.7 N isopropanolic hydrogen chloride, and the solid 5-iodo-2-[4-(3-thiazolidinyl)-butoxy]pyridine, monohydrochloride, that precipitates is isolated and crystallized twice from isopropanol; m.p. 165°–167° C.

EXAMPLE 6

Utilizing a procedure that is analogous to those described in Examples 1, 2, and 5 above, the following 2-[ω-(3-thiazolidinyl)alkoxy]pyridine compounds are obtained from the reactions indicated below.

(a) 5-Iodo-2-{[5-(3-thiazolidinyl)pentyl]oxy}-pyridine, monohydrochloride, m.p. 173°–175° C., following crystallization from ethanol; from the initial reaction of 12 g. of 2-{[5-(1-aziridinyl)pentyl]oxy}-5-iodopyridine with 3.7 g. of hydrogen sulfide in ethanol, and the subsequent reaction of the intermediate 2-{{5-[(5-iodo-2-pyridyl)oxy]pentyl}amino}ethanethiol with 48 g. of sodium formaldehyde bisulfite in aqueous methanol to give the free base product, which is further reacted in ether solution with 2.3 N isopropanolic hydrogen chloride to give the monohydrochloride salt.

(b) 5-Iodo-2-{[6-(3-thiazolidinyl)hexyl]oxy}-pyridine, monohydrochloride, m.p. 149°–152° C., following two crystallizations from ethanol; from the initial reaction of 9.9 g. of 2-{[6-(1-aziridinyl)hexyl]oxy}-5-iodopyridine with 3 g. of hydrogen sulfide in ethanol, and the subsequent reaction of the intermediate 2-{{6-[(5-iodo-2-pyridyl)oxy]hexyl}amino}ethanethiol with 39 g. of sodium formaldehyde bisulfite in aqueous methanol to give the free base product, which is further reacted in ether solution with 4.4 N isopropanolic hydrogen chloride to give the monohydrochloride salt.

(c) 5-Iodo-2-{[7-(3-thiazolidinyl)heptyl]oxy}-pyridine, monohydrochloride, m.p. 160°–163° C., following crystallization from isopropanol; from the initial reaction of 18.5 g. of 2-{[7-(1-aziridinyl)heptyl]oxy}-5-iodopyridine with 5 g. of hydrogen sulfide in ethanol, and the subsequent reaction of the intermediate 2-{{7-[(5-iodo-2-pyridyl)oxy]heptyl}amino}ethanethiol with 60 g. of sodium formaldehyde bisulfite in aqueous methanol to give the free base product, which is further reacted in ether solution with 4.7 N isopropanolic hydrogen chloride to give the monohydrochloride salt.

EXAMPLE 7

Utilizing a procedure that is analogous to those described in Examples 1, 2, and 5 above, from the initial reaction of 15 g. of 2-{[5-(1-aziridinyl)pentyl]oxy}-5-methylpyridine with 6.8 g. of hydrogen sulfide in ethanol, and the subsequent reaction of the intermediate 2-{{5-[(5-methyl-2-pyridyl)oxy]pentyl}amino}ethanethiol with 91 g. of sodium formaldehyde bisulfite in aqueous methanol, there is obtained 5-methyl-2-{[5-(3-thiazolidinyl)pentyl]-oxy}pyridine, which is isolated as the dihydrochloride salt by treating an ethereal solution of the free base with 29.6 ml. of 2.3 N isopropanolic hydrogen chloride and isolating the solid salt that precipitates; m.p. 164°–167° C., following crystallization from ethanol.

STARTING MATERIALS

The various starting materials required for use in the foregoing examples and intermediates therefor are prepared as described in the following.

A. (1-Aziridinyl)alkanols.

(1) 5-(1-Aziridinyl)-1-pentanol. A mixture consisting of 439 g. of 5-chloro-1-pentanol, 1030 g. of ethylenimine, 592 g. of powdered potassium carbonate, and 3 liters of ethanol is heated under reflux for 48 hours, cooled to room temperature, and diluted with 1 liter of chloroform. The mixture is filtered to remove the isoluble materials, and the filtrate is concentrated under reduced pressure to remove the solvent. The residue, which is the desired 5-(1-aziridinyl)-1-pentanol, is purified by distillation under reduced pressure; b.p. 112°–118° C./10 mm. Hg.

(2) 3-(1-Aziridinyl)-1-propanol, b.p. 80°–86° C./13 mm. Hg; obtained by the method of (1) above from the reaction of 94.5 g. of 3-chloro-1-propanol, 345 g. of ethylenimine, and 152 g. of powdered potassium carbonate in 1250 ml. of anhydrous ethanol.

(3) 4-(1-Aziridinyl)-1-butanol. A mixture consisting of 21 g. of 4-chloro-1-butanol, 33 g. of potassium carbonate, and 250 ml. of ethanol is stirred at room temperature until alkaline to litmus paper and is then treated with 64.5 g. of ethylenimine. The resulting mixture is stirred and heated under reflux for 3 days, cooled to room temperature, and diluted with chloroform. It is then filtered and the filtrate is concentrated under reduced pressure to remove the solvent. The residue, which is the desired 4-(1-aziridinyl)-1-butanol, is purified by distillation under reduced pressure; b.p. 94°–102° C./13 mm. Hg.

(4) 6-(1-Aziridinyl)-1-hexanol, b.p. 135°–150° C./25 mm. Hg; obtained by the method of (1) above from the reaction of 100 g. of 6-chloro-1-hexanol, 250 g. of ethylenimine, 110 g. of powdered potassium carbonate, and 1 liter of anhydrous ethanol.

(5) 7-(1-Aziridinyl)-1-heptanol. A mixture consisting of 300 ml. of ethylenimine, 115 g. of anhydrous potassium carbonate, 120 g. of 7-chloro-1-heptanol, and 750 ml. of anhydrous ethanol is heated under reflux for 72 hours, cooled to room temperature, and diluted with ether. The ethereal mixture is filtered through diatomaceous earth (Celite), and the filtrate is evaporated under reduced pressure. The residue is redissolved in ether, the ethereal solution is again filtered, and the filtrate is evaporated to dryness to give an oily residue of the desired 7-(1-aziridinyl)-1-heptanol, which is purified by distillation under reduced pressure; b.p. 82°–85° C./0.2 mm. Hg.

(6) 8-(1-Aziridinyl)-1-octanol, b.p. 94°–97° C./0.4 mm. Hg; obtained by the method of (5) above from the reaction of 127 g. of 8-chloro-1-octanol, 198 g. of ethylenimine, 117 g. of anhydrous potassium carbonate, and 1 liter of anhydrous ethanol.

B. 2-[(1-Aziridinyl)alkoxy]pyridines.

(1) 2-[3-(1-Aziridinyl)propoxy]-5-bromopyridine. To a suspension of 6.6 g. of a 55% sodium hydride in mineral oil dispersion in 190 ml. of tetrahydrofuran, heated under reflux, is slowly added 15.2 g. of 3-(1-aziridinyl)-1-propanol, and the resulting mixture is heated under reflux for 90 minutes. 2,5-Dibromopyridine (35.6 g.) is added and the reaction mixture is heated under reflux for 4 hours more, cooled, and diluted with 200 ml. of ether. The ethereal mixture is filtered through diatomaceous earth (Celite), and the filtrate is evaporated under reduced pressure. The residue is mixed well with 400 ml. of ether, the ethereal mixture is filtered, and the filtrate is evaporated to give a residue of the desired 2-[3-(1-aziridinyl)propoxy]-5-bromopyridine, which is purified by distillation under reduced pressure; b.p. 100°–106° C./0.1 mm. Hg.

(2) 2-[4-(1-Aziridinyl)butoxy]-5-bromopyridine, b.p. 100°–105° C./0.08 mm. Hg; obtained by the method of (1) above from the reaction of 11 g. of 4-(1-aziridinyl)-1-butanol with 22.7 g. of 2,5-dibromopyridine in the presence of 3.8 g. of a 60% sodium hydride in mineral oil dispersion in 150 ml. of tetrahydrofuran.

(3) 2-{[5-(1-Aziridinyl)pentyl]oxy}-5-bromopyridine, b.p. 109°–118° C./0.005 mm. Hg; obtained by the method of (1) above from the reaction of 27.3 g. of 5-(1-aziridinyl)-1-pentanol with 50 g. of 2,5-dibromopyridine in the presence of 9.3 g. of a 55% sodium hydride in mineral oil dispersion in tetrahydrofuran.

(4) 2-{[6-(1-Aziridinyl)hexyl]oxy}-5-bromopyridine, b.p. 140°–145° C./0.5 mm. Hg; obtained by the method of (1) above from the reaction of 18.2 g. of 6-(1-aziridinyl)-1-hexanol with 30 g. of 2,5-dibromopyridine in the presence of 5.06 g. of a 60% sodium hydride in mineral oil dispersion in tetrahydrofuran.

(5) 2-{[7-(1-Aziridinyl)heptyl]oxy}-5-bromopyridine, b.p. 125°–130° C./0.1 mm. Hg; obtained by the method of (1) above from the reaction of 19.1 g. of 7-(1-aziridinyl)-1-heptanol with 23.7 g. of 2,5-dibromopyridine in the presence of 4.2 g. of a 57% sodium hydride in mineral oil dispersion in tetrahydrofuran.

(6) 2-{[8-(1-Aziridinyl)octyl]oxy}-5-bromopyridine, b.p. 157°–163° C./0.3 mm. Hg; obtained by the method of (1) above from the reaction of 14.5 g. of 8-(1-aziridinyl)-1-octanol with 20 g. of 2,5-dibromopyridine in the presence of 3.4 g. of a 60% sodium hydride in mineral oil dispersion in tetrahydrofuran.

(7) 2-[4-(1-Aziridinyl)butoxy]-5-chloropyridine, b.p. 97° C./0.1 mm. Hg; obtained by the method of (1) above from the reaction of 23 g. of 4-(1-aziridinyl)butanol with 30 g. of 2,5-dichloropyridine in the presence of 8 g. of a 60% sodium hydride in mineral oil dispersion in tetrahydrofuran.

(8) 2-{[5-(1-Aziridinyl)pentyl]oxy}-5-chloropyridine, b.p. 118°–122° C./0.2 mm. Hg; obtained by the method of (1) above from the reaction of 43.6 g. of 5-(1-aziridinyl)-1-pentanol with 50 g. of 2,5-dichloropyridine in the presence of 13.5 g. of a 60% sodium hydride in mineral oil dispersion in tetrahydrofuran.

(9) 2-{[6-(1-Aziridinyl)hexyl]oxy}-5-chloropyridine, b.p. 114°–117° C./0.05 mm. Hg; obtained by the method of (1) above from the reaction of 48.4 g. of 6-(1-aziridinyl)-1-hexanol with 50 g. of 2,5-dichloropyridine in the presence of 13.5 g. of a 60% sodium hydride in mineral oil dispersion in tetrahydrofuran.

(10) 2-[4-(1-Aziridinyl)butoxy]-5-iodopyridine, b.p. 115°–120° C./0.06 mm. Hg; obtained by the method of (1) above from the reaction of 11.6 g. of 4-(1-aziridinyl)-1-butanol with 28.4 g. of 2-bromo-5-iodopyridine in the presence of 4.2 g. of a 57% sodium hydride in mineral oil dispersion in tetrahydrofuran.

(11) 2-{[5-(1-Aziridinyl)pentyl]oxy}-5-iodopyridine, b.p. 135°–140° C./0.2 mm. Hg; obtained by the method of (1) above from the reaction of 12.9 g. of 5-(1-aziridinyl)-1-pentanol with 28.4 g. of 2-bromo-5-iodopyridine in the presence of 4 g. of a 60% sodium hydride in mineral oil dispersion in tetrahydrofuran.

(12) 2-{[6-(1-Aziridinyl)hexyl]oxy}-5-iodopyridine, b.p. 157°–163° C./0.05 mm. Hg; obtained by the method of (1) above from the reaction of 15.1 g. of 6-(1-aziridinyl)-1-hexanol with 30 g. of 2-bromo-5-iodopyridine in the presence of 4.5 g. of a 57% sodium hydride in mineral oil dispersion in tetrahydrofuran.

(13) 2-{[7-(1-Aziridinyl)heptyl]oxy}-5-iodopyridine. To a suspension of 4.2 g. of a 57% sodium hydride in mineral oil dispersion in 100 ml. of tetrahydrofuran is added a solution of 19.1 g. of 7-(1-aziridinyl)-1-heptanol, and the resulting mixture is heated under reflux for 90 minutes. Upon cooling to room temperature, a solution of 28.4 g. of 2-bromo-5-iodopyridine in 100 ml. of tetrahydrofuran is added, and the reaction mixture is again heated under reflux for 4 hours, cooled to room temperature, and filtered through diatomaceous earth. The filtrate is evaporated under reduced pressure, the residue is mixed well with ether, and the ethereal solution is also filtered through diatomaceous earth. The filtrate is evaporated under reduced pressure to give an oily residue of the desired 2-{[7-(1-aziridinyl)heptyl]oxy}-5-iodopyridine, which is isolated and purified by crystallization twice from iso-octane; m.p. 41°–45° C.

(14) 2-{[15-(1-Aziridinyl)pentyl]oxy}-5-methylpyridine, b.p. 112°–122° C./0.2–0.3 mm. Hg; obtained by the method of (1) above from the reaction of 51.6 g. of 5-(1-aziridinyl)-1-pentanol with 69 g. of 2-bromo-5-methylpyridine in the presence of 16 g. of a 60% sodium hydride in mineral oil dispersion in tetrahydrofuran.

I claim:

1. A member of the class consisting of 2-[ω-(3-thiazolidinyl)alkoxy]pyridine compounds having the formula

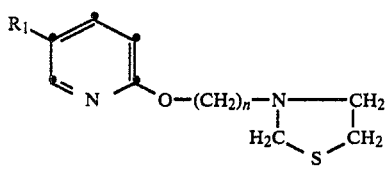

and pharmaceutically-acceptable salts thereof; where $R_1$ is a member of the class consisting of methyl, chlorine, bromine, and iodine, and n is a positive integer having a value of from 3 to 8, said $R_1$ and n being selected as follows: when $R_1$ is methyl, n is 5; when $R_1$ is chlorine, n is selected from among 4, 5, and 6; when $R_1$ is bromine, n is selected from among 3, 4, 5, 6, 7, and 8; and when $R_1$ is iodine, n is selected from among 4, 5, 6, and 7.

2. A compound according to claim 1 which is 5-bromo-2-{[6-(3-thiazolidinyl)hexyl]oxy}pyridine, monohydrochloride.

3. A compound according to claim 1 which is 5-chloro-2-{[5-(3-thiazolidinyl)pentyl]oxy}pyridine, dihydrochloride.

4. A compound according to claim 1 which is 5-chloro-2-{[6-(3-thiazolidinyl)hexyl]oxy}pyridine, monohydrochloride.

5. A compound according to claim 1 which is 5-iodo-2-{[5-(3-thiazolidinyl)pentyl]oxy}pyridine, monohydrochloride.

6. A compound according to claim 1 which is 5-iodo-2-{[6-(3-thiazolidinyl)hexyl]oxy}pyridine, monohydrochloride.

* * * * *